United States Patent
Feijtel (10) Patent No.: US 7,699,611 B2
(45) Date of Patent: Apr. 20, 2010

(54) FASTENING DEVICE FOR AN ORTHESIS OR PROSTHESIS

(75) Inventor: Jasper Feijtel, Dordrecht (NL)

(73) Assignee: Accius B.V., Goes (NL)

( * ) Notice: Subject to any disclaimer, the term of this patent is extended or adjusted under 35 U.S.C. 154(b) by 228 days.

(21) Appl. No.: 10/467,110

(22) PCT Filed: Feb. 5, 2002

(86) PCT No.: PCT/NL02/00083

§ 371 (c)(1),
(2), (4) Date: Dec. 2, 2003

(87) PCT Pub. No.: WO02/062257

PCT Pub. Date: Aug. 15, 2002

(65) Prior Publication Data

US 2004/0078040 A1    Apr. 22, 2004

(30) Foreign Application Priority Data

Feb. 5, 2001  (NL) .................................... 1017284

(51) Int. Cl.
*A61C 8/00* (2006.01)
(52) U.S. Cl. ...................... 433/173; 433/174
(58) Field of Classification Search .......... 433/172–176, 433/167, 193, 215, 201.1; 606/73; 623/16.11, 623/17.17
See application file for complete search history.

(56) References Cited

U.S. PATENT DOCUMENTS

| | | | |
|---|---|---|---|
| 4,062,119 A * | 12/1977 | Linkow et al. ............... 433/176 |
| 4,209,904 A | 7/1980 | Staubli | |
| 5,219,286 A * | 6/1993 | Hader ......................... 433/172 |
| 5,302,125 A * | 4/1994 | Kownacki et al. ........... 433/172 |
| 5,516,288 A | 5/1996 | Sichler et al. | |
| 5,588,838 A | 12/1996 | Hansson et al. | |
| 5,997,299 A * | 12/1999 | Unger ......................... 433/173 |
| 6,379,354 B1 * | 4/2002 | Rogozinski ................. 606/260 |

FOREIGN PATENT DOCUMENTS

| | | | |
|---|---|---|---|
| DE | EP 0393324 A1 * | 2/1990 |
| DE | 3841008 A1 * | 6/1990 |
| DE | 197 48 268 A1 | 5/1999 |
| EP | 0 393 324 | 10/1990 |
| EP | 0 534 456 A2 | 9/1992 |
| FR | EP1072228 A1 * | 7/1999 |

* cited by examiner

*Primary Examiner*—Ralph A Lewis
*Assistant Examiner*—Yogesh Patel
(74) *Attorney, Agent, or Firm*—Michaelson & Associates; Peter L. Michaelson; Peter A. Luccarelli, Jr.

(57) ABSTRACT

A device for fastening an orthesis or prosthesis, having a length-adjustable substantially rod-shaped bar assembly, which is pivotably connectable by two ends on exposed first ends of two implants fastened by a second end at a distance from each other in or onto a bone. With this bar assembly, a three-dimensional angle between the longitudinal axis of the bar assembly and the longitudinal axis of at least one implant can be set, so that, irrespective of the distance between and the relative position of the implants, each time, a fitting, preferably stress-free connection between these implants can be effected.

29 Claims, 5 Drawing Sheets

FASTENING DEVICE FOR AN ORTHESIS OR PROSTHESIS

BACKGROUND OF THE INVENTION

1. Field of the Invention

The invention relates to a device for fastening an orthesis or a prosthesis, comprising a substantially bar-shaped bar assembly, which is connectable by or adjacent to two extremities to exposed first ends of two implants fastened at a distance from each other by a second end in or onto a bone, while forming a rigid connection therebetween.

2. Description of the Relevant Art

Such devices are known from practice, in particular from dental surgery. On the bar-shaped part of the device, a prosthesis or orthesis can be detachably secured by means of one or more clamping elements. A problem in realizing such a device is that the position of the implants can differ per case, inter alia in that the position is substantially determined in situ, in vivo. Therefore, to realize a fitting connection between these implants, each bar assembly has to be separately manufactured to size. In practice, this is done by making an impression of a relevant part of the jaw, with the implants extending therein, whereupon, on the basis of this impression, in a laboratory, a bar assembly is manufactured, for instance by means of investment casting.

Having a bar assembly manufactured in a laboratory is time-consuming, expensive and, moreover, susceptible to trouble. At each manufacturing step, such as, for instance, the manufacture of an impression, a casting model and the final bar assembly, inaccuracies can be introduced, resulting in a bar assembly which does not perfectly fit the implants and which, when it is nevertheless secured thereto, will cause undesired stresses in the construction and the jaw. In practice, for this reason, a significant percentage of bar assemblies has to be rejected and the manufacturing steps described hereinabove have to be traversed again.

SUMMARY OF THE INVENTION

The invention contemplates a device of the type described in the opening paragraph, in which the drawbacks mentioned have been avoided.

A bar assembly according to the invention offers the advantage that it is adjustable. Thus, this bar assembly can be adapted such, in particular in length and orientation thereof relative to the implants, that, each time, this bar assembly can form a fitting and preferably stress-free connection between two adjacent implants, irrespective of the mutual distance, the possible difference in height and/or a possible skewness of these implants. Due to its universal applicability, such an adjustable bar assembly can be produced in relatively large quantities for sale and inventory. As a result, the manufacturing costs and delivery time can be considerably reduced compared to the known bar assemblies which are individually manufactured to size. Furthermore, time, material and manpower are saved as no preparatory operations have to be carried out, such as, for instance, the repeated manufacture of a jaw impression. Finally, the chance of success for creating a stress-free connection is high, as the bar assembly unambiguously sets to the position of the implants. Due to this unambiguousness, upon detaching and re-fastening, the bar assembly will take on exactly the same position.

Use of a coupling element between each implant and the bar assembly offers the advantage that the same bar assembly can be used with various types of implants. To that end, only a different coupling element needs to be used, an end of which proximal to the implant is tailored to the form and dimensions of the free end of the respective type of implant, so that, in fastened position, both ends preferably seamlessly connect to each other. As a result, with a minimum of different parts, a flexibly usable bar assembly can be obtained.

By providing the sides proximal to each other in the fastened position of, on the one hand, the coupling element and the extremity of a bar arm, and, on the other hand, the facing sides of the fastening screw and the extremity of the bar arm with forms which are pivotable relative to each other, the bar arm, and hence the bar assembly, can be positioned and fastened in any desired position relative to the coupling element and the implant located underneath. Thus, a desired or undesired inclination of one or both implants relative to the bone to or in which they have been fastened can be compensated by appropriately pivoting the or each respective extremity of the bar assembly and a straight, stress-free connection between these implants can be effected.

Each extremity of the bar assembly is, in combination with the accompanying coupling element and the fastening screw, preferably designed such that a connection is obtained which is form-closed in one or several desired directions, so that in those respective directions no movements are allowed, while the connection is freely adjustable in the other directions.

As the bar assembly is detachably fastened with the screw on the implants, the bar assembly, if required, can at all times be removed in a simple manner, and parts thereof can be replaced.

Preferably, the or each extremity of the bar assembly is shaped such that it can be pivotally received in and/or adjacent to the extremity of a second bar assembly. Thus, two extremities of two different bar assemblies can, together, be fastened on one implant in a compact manner, while the positions of the two bar assemblies can be set independently of each other. In this manner, a series of bar assemblies can be linked, while, each time, each bar assembly can form a stress-free connection between a successive pair of implants. Such a linkage of bar assemblies offers more fastening possibilities for a prosthesis and an even better, more even support thereof.

The invention also relates to a model of a jaw part having a device according to the invention.

Such a model can serve for training purposes, for instance in fitting and securing a bar assembly to two implants. Furthermore, with the aid of such a model, the clamping elements can be provided at a suitable position and at a proper angle in the prosthesis or orthesis.

Further advantageous embodiments of a device according to the invention, a model thereof, an assembly of a device and a prosthesis and a method for realizing a device according to the invention are described and recited in the claims.

BRIEF DESCRIPTION OF THE DRAWINGS

In elucidation of the invention, an exemplary embodiment of a device will be described with reference to the drawing. In the drawing.

DETAILED DESCRIPTION OF THE INVENTION

In this description, identical or corresponding parts have identical or corresponding reference numerals.

Figure 1:
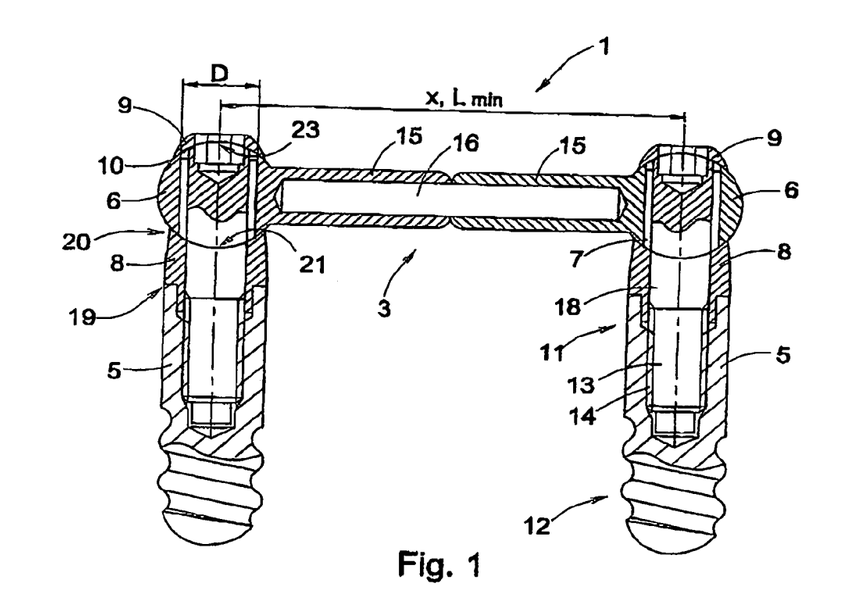
FIG. 1 shows a cross section of a device for fastening an orthesis or prosthesis according to the invention.

FIG. 1 shows a device according to the invention for fastening an orthesis or prosthesis, comprising two implants 5 which are mutually connected by an elongated linear element bar assembly 3. Here, the length of the bar assembly 3 and the angle between the longitudinal axis of the bar assembly 3 and the longitudinal axes of the implants 5 is adjustable such, that herewith, irrespective of the location and the orientation of the implants 5, a fitting and therefore stress-free connection can be effected. Then, onto this connection, a prosthesis or orthesis can be detachably fitted with the aid of clamping elements 50 (see FIG. 2) known per se. To simplify the description, in the following, there, where an orthesis and/or prosthesis are concerned, only a prosthesis will be mentioned.

What is meant in this context by implant 5 is a pin-shaped, plate-shaped or still other-shaped element which is connected by a second end 12 to or in a bone of for instance an upper or lower jaw, and which faces the oral cavity with a first end 11. Such implants 5 are known from practice and available in various types and sizes, mutually differing in, among others, shape, length, diameter and the manner of fastening in or to the bone. Thus, for instance, the second end 12 can be screwed into a bone, cemented therein or be fastened by means of a so-called 'push in' technique. With the latter method, the implant 5 is treated with a special coating and then pushed into a pre-drilled hole. The coating enables the bone, in time, to grow together with the implant 5, so that a strong connection is formed. For the purpose of fastening the bar assembly 3, in a manner to be described further, the exposed first end of the implants 5 is provided with a blind hole 13 with interior screw thread 14.

The bar assembly 3 is built up from two substantially tubular elements, hereinafter called bar arms 15, and a bar rod 16, which is slideably received with at least one end in the bar arms 15. As a result, the length L of the bar assembly 3 can be varied between a minimum value $L_{min}$, as shown in FIG. 1, where the bar rod 16 is complete received in the bar arms 15, and a maximum value $L_{max}$ (not shown), where the bar arms 15 have been shifted adjacent the extremities of the bar rod 16. At the sides remote from each other, the bar arms 15 are each provided with a ball-shaped extremity 6 in which, approximately at right angles to the longitudinal axis of the bar arm 15, a continuous bore 7 extends with a circular or preferably oval cross section. Through this bore 7, a fastening screw 9 can be provided, with which the ball-shaped extremity 6 can be secured on the implant 5.

In the embodiment shown in FIG. 1, between the ball-shaped extremity 6 and the implant 5, a coupling element 8 has been arranged which provides for a fitting transition between the implant 5 and the bar assembly 3. To that end, the coupling element 8 comprises a first end 19 which accurately connects to the free first end 11 of the implant 6 and a second end 20, forming a socket 21, at least a part thereof, in which the ball-shaped extremity 6 can fittingly lie in a pivotable manner. For the passage of the fastening screw 9, the coupling element 8 is provided with a continuous hole 18. At a side proximal to the ball-shaped extremity 6 during use, the screw 9 is provided with a second socket 23 which can fittingly abut against the side of the ball-shaped extremity 6 remote from the coupling element 8, for pivotally confining it. Due to the thus shaped ball-and-socket joint, the bar arm 15 can be pivoted in any desired position relative to the implant 5, and a desired angle φ between the longitudinal axes of the bar arm and an implant can be set.

Per different type of implant 5, a specific coupling element 8 can be manufactured, the first end 19 (see FIG. 1) thereof being adapted to the geometry of the exposed end 11 of the respective implant 5. The second end 20, proximal to the bar assembly 3, is preferably identical for each coupling element 8. As a result, for each type of implant 5 the same bar assembly 3 can be used and preferably also the same fastening screw 9. This enlarges the field of application of the bar assembly 3 and makes allows it to be manufactured in large quantities and, therefore, in a relatively inexpensive manner. Furthermore, such a generally usable assembly 8 can be manufactured for stock, so that waiting times can be minimized. As, per different type of implant 5, only the coupling element 8 and, possibly, the fastening screw 9 need to be adapted, thus reducing the number of different parts to a minimum.

FIG. 1 shows an example of a device 1 according to the invention, wherein two implants 5 are anchored in a jaw bone parallel to each other at a mutual distance x. To realize a fitting, stress-free connection between these implants 5 and the coupling elements 8 provided thereon, the bar arms 15 have been shifted towards each other over the bar rod 16 before provision on the implants 5 such, that the ball-shaped extremities 6 of the bar assembly precisely fall into the socket-shaped ends 20 of the coupling elements 8. In the example shown, the distance x between the implants 5 corresponds to the minimum length $L_{min}$ the bar assembly can adopt, with the bar arms 15 shifted towards each other maximally. When the distance x between two implants 5 is greater than in the case shown in FIG. 1, and, therefore, a longer connection between the implants 5 is required, the same bar assembly 3 can be used by shifting the bar arms 15 apart along the bar rod 16, until the length L of the bar assembly 3 corresponds to the distance x between the free ends 11 of the implants. In this manner, with the same bar assembly 3, a range of distances x between two implants 5, differing per case can be bridged.

Figure 2:
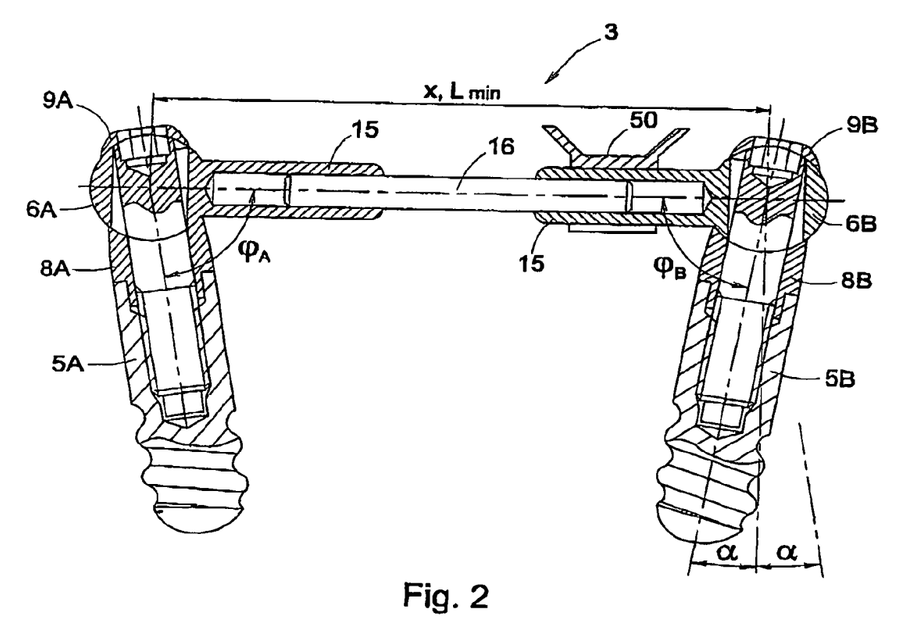
FIG. 2 shows a cross section of the device of FIG. 1 with skew implants.

In FIG. 2, a situation often occurring in practice is shown, wherein the implants 5 are anchored in a bone at an angle α. For fastening, in this case, the bar assembly 3 fittingly on the implants 5, both the length L of the bar assembly 3 and the angles φ between the longitudinal axes of the bar arms 15 and the implants 5 need to be adjusted. To that end, the bar assembly 3 is pivotably fastened with a first ball-shaped extremity 6A onto a first coupling element 8A by means of a first fastening screw 9A. The, by shifting apart one or both bar arms 15 along the bar rod 16, the bar assembly 3 is lengthened such that the second ball-shaped extremity 6B falls exactly in the socket of the second coupling element 8B. Simultaneously, by pivoting the ball-shaped extremities 6A, 6B relative to the coupling elements 8A, 8B, the angles $φ_a$ and $φ_b$ between the longitudinal axes of the bar assembly 3 and the respective implants 5A, 5B are adjusted, so that the bar assembly 3 forms a straight connection between the implants 5A, 5B. Then, the second extremity 6B is secured onto the implant 5B with a second fastening screw 9B. As the thus formed connection consists of parts freely moveable relative to each other and which cannot absorb forces in their direction of movement, the connection is guaranteed to be stress-free.

Optionally, the parts of the bar assembly 3 can be fixed in this stress-free position, naturally without the setting being disturbed. This can be done, for example, by filling the space between the bar arm 15 and the bar rod 16 with bone cement, or by gluing the parts together, clamping them onto each other by mechanical deformation or by using memory metal in strategic places. It is also possible to already fix a part of the parts of the bar assembly prior to fitting the bar assembly. For instance, as soon as the distance x between the implants to be maximally bridged is at least approximately known, one of the bar arms 15 can already be secured to an end of the bar rod 16, for instance by means of soldering or one of the fastening methods mentioned hereinabove. This offers the advantage that a more rigid construction can be obtained, wherein, furthermore, the position of the bar rod 16 relative to the bar arms 15 is unequivocally determined. Naturally, it should be provided that the remaining slideable bar arm 15 can furnish the change in length required for adjusting the proper angle φ between the bar assembly 3 and the implants 5.

The fastening device for a prosthesis realized with a bar assembly 3 according to the invention is compact and streamlined, without sharp or projecting edges. It is noted, for that matter, that the connection need not be straight, but can have any desired different shape, for instance a curved shape, following the jaw line. All parts are well accessible for the purpose of cleaning and maintenance and preferably detachably connected to each other, so that they can be easily replaced in case of wear or damage. The device 1 is manufactured from a durable material, such as, for instance, an alloy of titanium or a different material proven suitable in practice for use in the human body. The prosthesis can be snapped tight onto the bar assembly 3, in particular onto the tubular part of the bar arms 15, with the aid of clamping elements 50 known from practice, for, for instance, false teeth, as shown at the right hand side in FIG. 2. With the aid of an impression or model of the jaw, with, therein, a model of the bar assembly 3, these clamping elements 50 can be provided at the right position and at the right angle in the prosthesis.

Figure 3A:
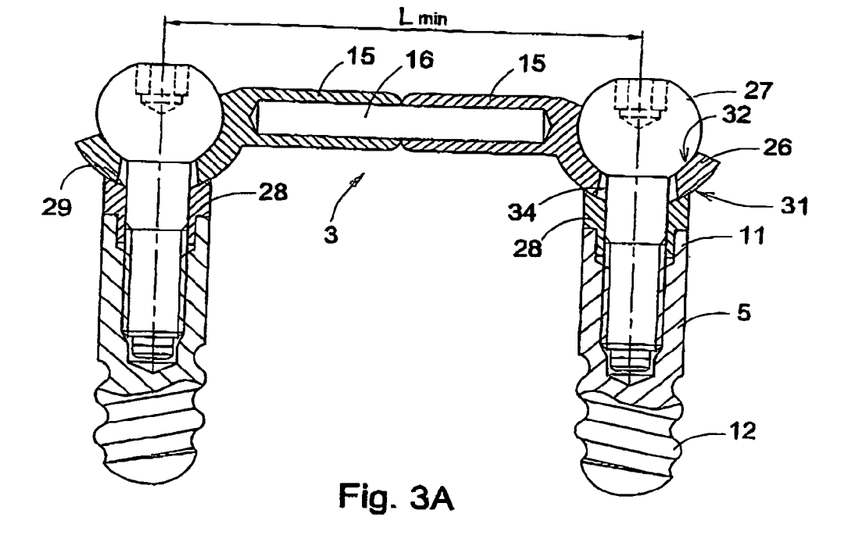
FIGS. 3a, b show a cross section of a second embodiment of a device according to the invention, applied to straight and skew implants.
Figure 3B:
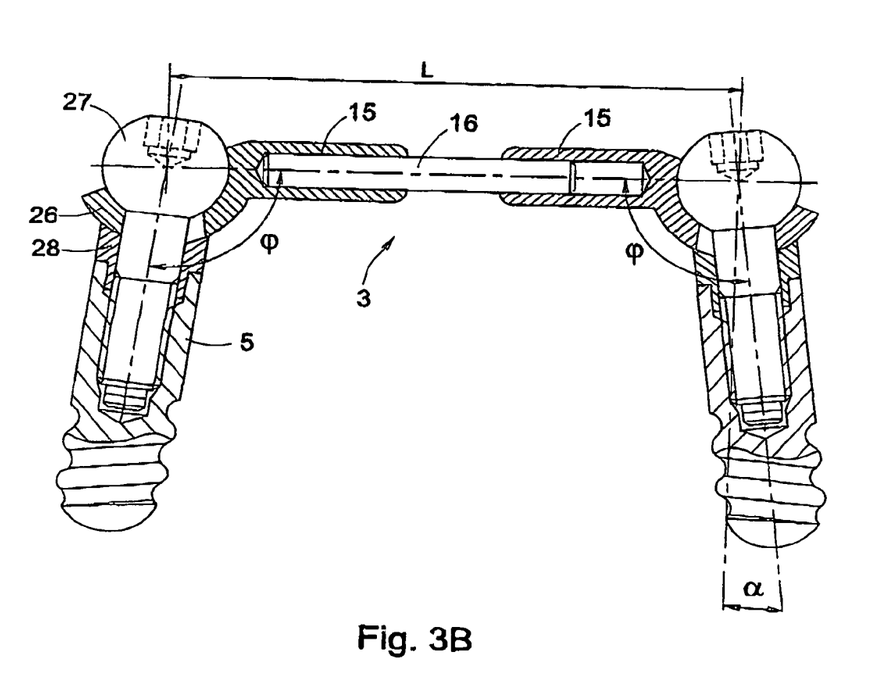

In FIGS. 3A and 3B, a second embodiment of a device 1 according to the invention is shown. The device 1 comprises a bar assembly 3 which is secured on two implants 5, with the aid of coupling elements 28 and fastening screws 27. The bar assembly 3 comprises, as the embodiment shown in FIG. 1, two substantially tubular bar arms 15 which are slideably arranged on two ends of a bar rod 16. The extremities 26 of these bar arms 15 have a ball-shaped side 31 proximal to the implant 5, and a socket-shaped side 32 proximal to the fastening screw 27. Further, each extremity 26 is provided with a conical hole 34, for the passage of the fastening screw 27. The coupling element 28 and the fastening screw 27 together enclose a space in which the extremity 26 of the bar assembly 3 can be pivotally received. To that end, the fastening screw 27 is provided with a ball-shaped head cooperating with the socket-shaped side 32 of the bar arm end 26, and the coupling element 28 has a socket-shape cooperating with the ball-shaped side 31 of the bar arm end 26. This embodiment offers the advantage that the different parts, in particular the fastening screws 27, can be manufactured in a very simple manner.

In a manner corresponding to the embodiment shown in FIG. 2, the bar assembly 3 can be provided stress-free between the implants 5 by adjusting the length L and angle φ, as shown in FIG. 3B. Preferably, prior to this provision, one bar arm 15 is fixedly connected to the bar rod 16, as shown at the left hand side in FIG. 3B. As a result, the position of the bar rod 16 after fastening the bar assembly 3 onto the implants 5 is unequivocally defined and an even more rigid bar assembly 3 is obtained.

As to length L, the maximum adjustability of the bar assemblies 3 shown in FIGS. 1-3 is determined by the length of the bar arms 15 in combination with the length of the bar rod 16 and, as to the angle φ, the maximum adjustability is limited by the play between the bore 7, 34 and the shaft of the fastening screw 9, 27. Thus, the maximum skewness α to be compensated, the maximum difference in height between two ends 11 to be compensated, and the minimum and maximum distance $L_{min}$, $L_{max}$, to be bridged are determined. Optionally, a number of categories of bar assemblies 3 can be manufactured, wherein the length and play mentioned vary, so that, per category, a particular maximum length L and angle φ can be set. The bores 7, 34 in the extremities 6, 26 of the bar arms 15 (FIGS. 1-3) preferably have an oval cross section. As a result, a partly form-closed connection is obtained, wherein the angle φ between the bar arms 15 and the implants 5 can be freely adjusted and the extremities 6, 26 can rotate freely about the longitudinal axis of an underlying coupling element 8, 28, but wherein rotation of the extremities 6, 26 (mentioned) about the longitudinal axis of the bar arms 15 is precluded. As a result, the bar assembly 3 can, each time, be fittingly secured on the implants 5 in one manner. Furthermore, such a form-closed connection helps prevent the fastening screws 9, 27 from coming loose during use.

Figure 4A:
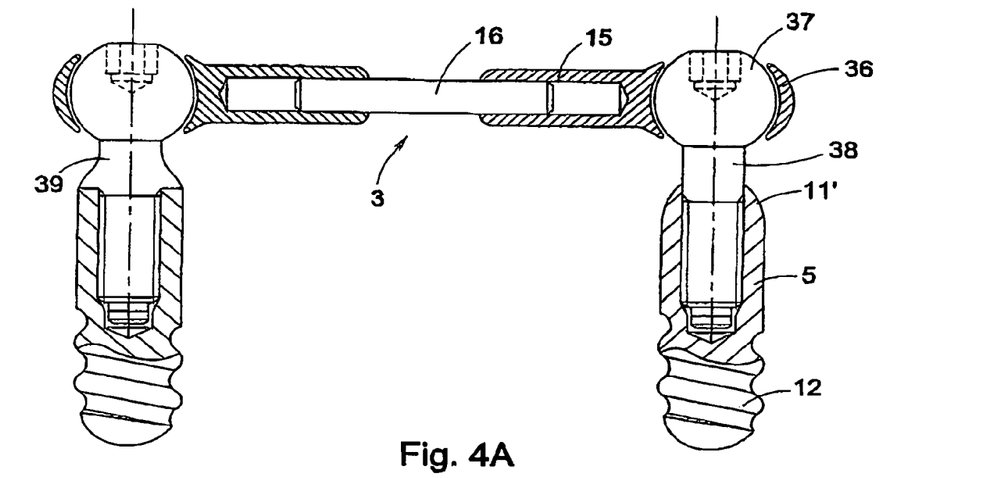
FIGS. 4a, b show a cross section of a third embodiment of a device according to the invention, in two different positions.
Figure 4B:
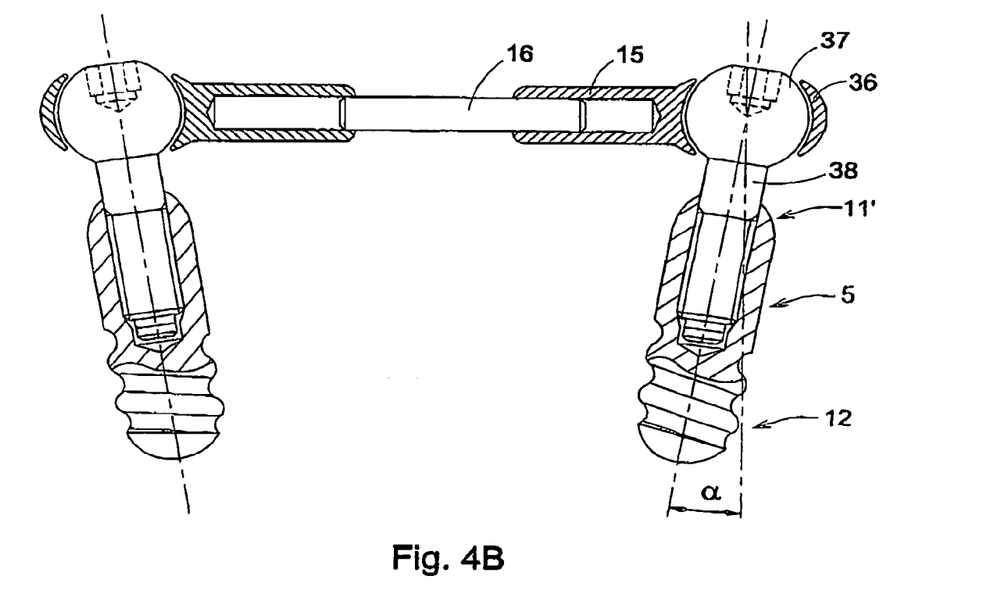

In FIGS. 4A and 4B, a third embodiment of a device 1 according to the invention is shown, wherein FIG. 4A shows a situation in which the implants 5 are both provided in the bone in a straight manner and FIG. 4B shows a situation in which the implants 5 are at an angle α. Like the previous embodiments, the bar assembly 3 comprises two substantially tubular bar arms 15, slid on opposite sides on a bar rod 16, and with which the length L of the bar assembly 3 can be varied between a minimum and maximum value $L_{min}$, $L_{max}$. Each bar arm 15 is provided with a ring-shaped end 36, provided around a ball-shaped head 37 of a fastening screw 38. Here, the shape and dimension of the ring 36 are such that this cannot be detached from the head 37, but can pivot freely relative to this head 37, so that a desired angle φ between the longitudinal axes of the bar arm 15 and the implant 5 can be set. An advantage of this embodiment is that the angle φ is adjustable over a relatively large range, so that this bar assembly is very suitable for use with implants 5 with a large skewness α. Furthermore, the bar assembly 3 can be directly fastened to the implants 5 with the screws 38, without interposition of a coupling element. To have the implant 5 and the fastening screw 38 connect seamlessly to each other, either the fastening screw 38 can be provided with a modified middle part 39, as shown at the left hand side in FIG. 4A, or the implant 5 can be provided with a rounded-off end 11', as shown on the right hand side. As the coupling element is omitted, the arrangement can be mounted still more simply and, further, the costs for manufacture can be even further reduced.

Figure 5A:
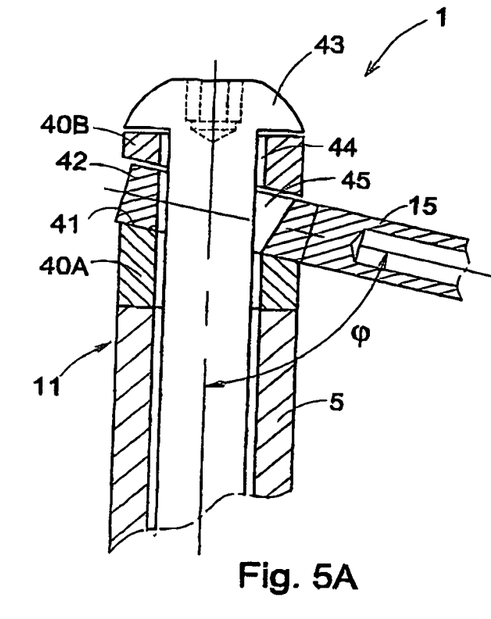
FIGS. 5a, b, c show a cross section of a fourth embodiment of a device according to the invention, in three different positions.
Figure 5B:
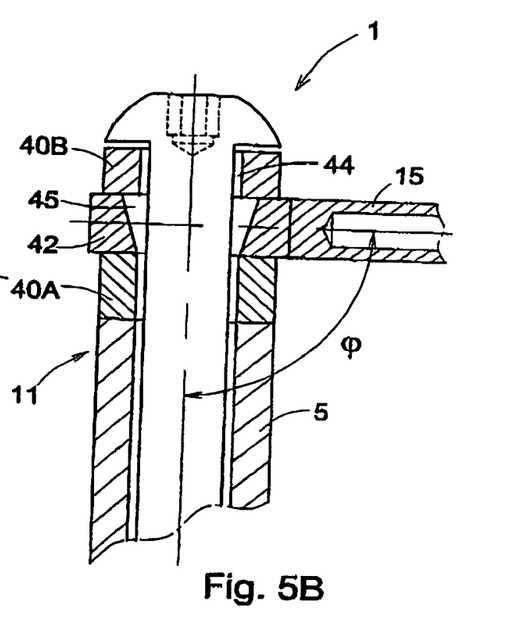
Figure 5C:
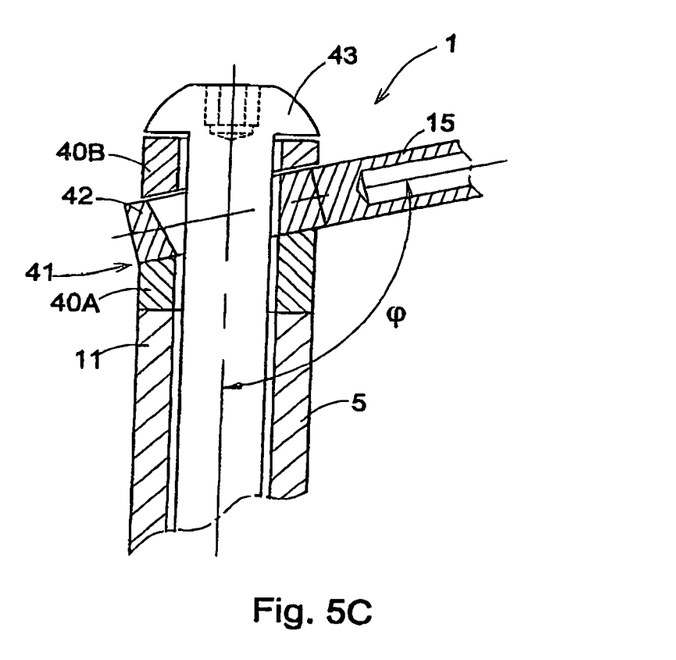

FIGS. 5A-5C show a fourth embodiment of the device 1, at least a half thereof, wherein the angle φ between the longitudinal axes of the bar arm 15 and an implant 5 can be set with the aid of a cylindrical coupling element 40, divided in two halves 40A, 40B along a diagonal separation surface 41. The bar arm 15 is provided with a disc-shaped end 42, which is secured on the implant 5 between the two halves 40A, B of the coupling element 40 with the aid of a fastening screw 43. For the passage of this fastening screw 43, both coupling element halves 40A, B are provided with a through hole 44 and the end 42 of the bar arm 15 is provided with a tapering hole 45, the smallest diameter of which is equal to the diameter of the hole 44 in the coupling element halves 40A, B. The angle φ between the bar arm 15 and the implant 5 can be varied by rotating both halves 40A, B simultaneously about their longitudinal axis. This is illustrated in FIGS. 5A-5C. FIG. 5A shows a first extreme position in which the bar arm 15 includes a minimum angle $\phi_{min}$ with the implant 5. By rotating the halves 40A, B from this position over 90°, the inclining side 41, depending on the direction of rotation, comes to lie forward or backward, out of the plane of the drawing. This is represented in FIG. 5B. The disc-shaped end 42 is then slightly pivoted about the longitudinal axis of the implant 5 and the bar arm 15 includes a right angle with the longitudinal axis of the implant 5. In this position, the bar assembly 3 is therefore suitable to be fastened on two implants 5 which are anchored at a right angle in a bone. When, starting from FIG. 5B, the coupling element halves 40A, B are again rotated over 90°, the bar arm 15 will pivot to a second extreme position, wherein the bar arm 15 includes a maximum angle $\phi_{max}$ with the implant 5, as shown in FIG. 5C. From FIGS. 5A and 5C it also becomes apparent why the hole 45 in the bar arm end 42 tapers. Without such a tapering configuration, the passage for the fastening screw 43 in the extreme positions would be too narrow. By subsequently rotating the halves 40A, B another quarter turn, a comparable situation is obtained as shown in FIG. 5B, wherein the bar arm 15 is substantially at right angles to the longitudinal axis of the implant 5 and the disc-shaped end 42 is tilted somewhat around the longitudinal axis of the bar arm 15. Finally, the halves 40A, B can, again, be rotated over 90°, thereby returning the bar arm 15 to the position as shown in FIG. 5A. In this manner, any angle φ between the minimum and maximum value $\phi_{min}$, $\phi_{max}$ can be set. This minimum and maximum angle $\phi_{min}$, $\phi_{max}$ depend on the gradient of the diagonal plane of separation 41; the steeper the plane, the larger the range to be set and, therefore, the larger the skewness of the implants 5 to be maximally compensated.

To prevent a user from hurting himself on the angular transitions which may occur in this embodiment between the end 42 of the bar arm 15 and the coupling element halves 40A, B (as is apparent from, for example, FIGS. 5a and 5c), the parts mentioned can be covered with a protective hood (not shown).

Figure 6:
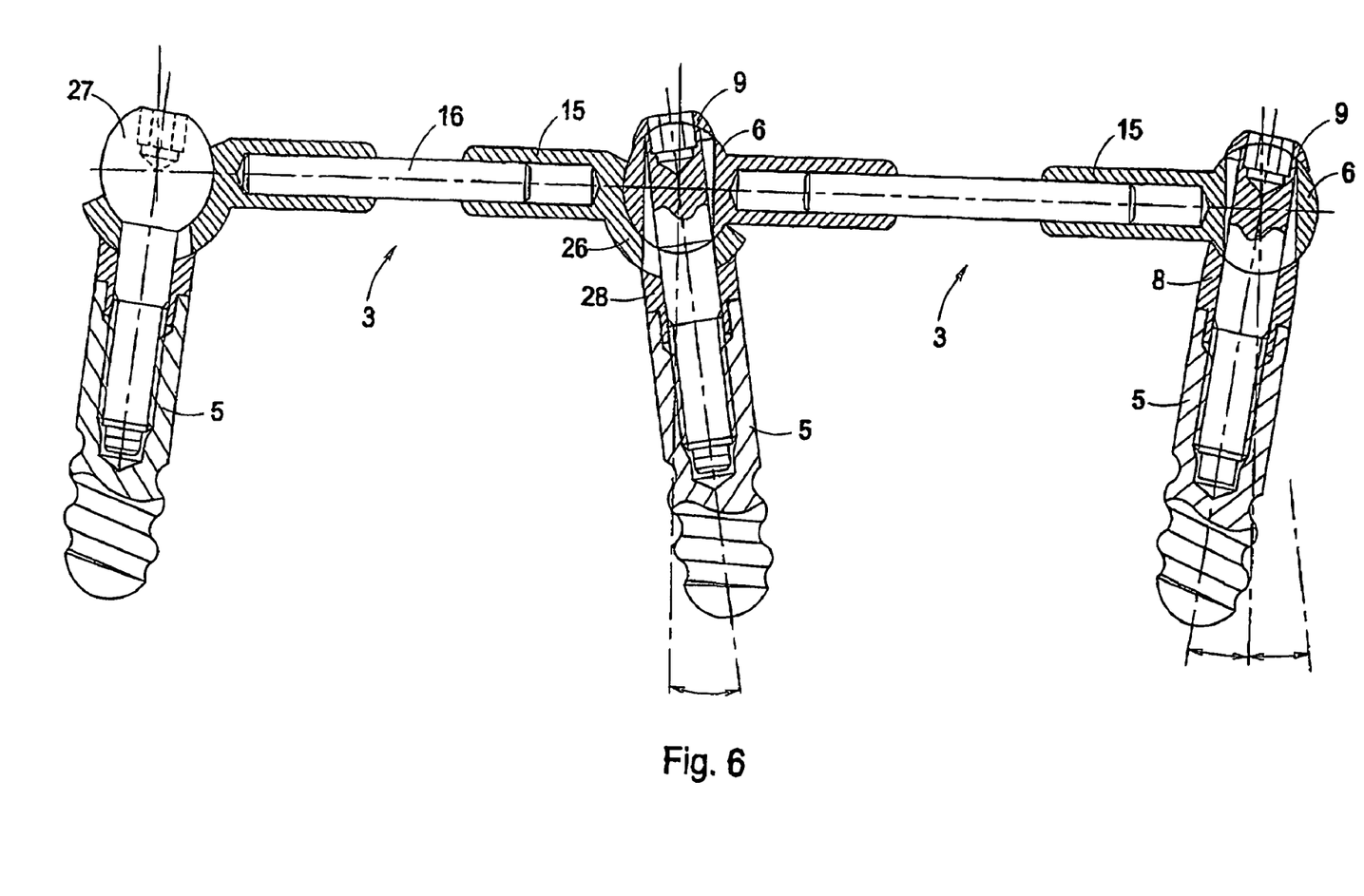
FIG. 6 shows a cross section of two linked devices according to the invention.

Finally, in FIG. 6, a number of linked bar assemblies 3 are shown, wherein two ends 6 of two different bar assemblies 3 are fastened on one implant 5. To that end, these ends 6 have a form cooperating with each other and with the coupling piece 8 and the fastening screw 9 such, that both ends 6 can pivot relative to each other, so that the position of each bar assembly 3 can be set separately. In this manner, a series of bar assemblies 3 can be coupled to each other, for instance while following the jaw line. Thus, a still larger fastening surface for the prosthesis is formed and it can be supported even better. It is also possible to arrange several prostheses next to each other.

The invention is not limited in any manner to the exemplary embodiments represented in the description and the drawings. Many variations thereon are possible within the framework of the invention as outlined by the claims.

For instance, the device is not limited to dental applications, but it is also suitable for orthopedic uses in general. To that end, for instance the dimensions of the device, the number of fastening devices per orthesis or prosthesis and the shape of the implants and the bar assembly can be adjusted to wish. It is also possible to effect a connection with the device in which, conversely, a particular desired stress is induced, so that two parts to be connected to each other can be held together or, conversely, apart with a particular force. This can, for instance, be favorable with bone fractures, where a bone is to be stretched or, conversely, has to be pressed onto a second bone part with a particular force. In that case, with the device according to the invention, a connection between the respective parts can be effected, whereupon in this connection, a compressive or tensile strength can be induced, for instance by means of a screw connection between the bar rod and one or both bar arms.

The bar assembly may comprise one bar arm instead of two, which one bar arm is slideably arranged on a first end of a bar rod. The other end of the bar rod may, in that case, be provided with one of the shapes described hereinabove such as a socket, a ball, or a flat ring with which this end can be pivotably connected to an implant. Instead of a bar rod, a bar sleeve can be used, in which solid or non-solid bar arms can be slideably received. Further, between the two ends of the bar assembly and the implants, instead of ball joints, line joints can be formed, a pivot axis of which extends at right angles to the plane through the longitudinal axes of the bar assembly and the implants.

These and many variations are understood to fall within the framework of the invention as outlined by the claims.

The invention claimed is:

1. A device for fastening a dental prosthesis to two dental implants, comprising:
    a substantially rod-shaped bar assembly with first and second opposing ends and having:
        first and second connecting elements respectively situated at the first and second ends; and
        a rod-shaped element situated between and slideably engaging by direct axial motion with each of the connecting elements; and
    wherein:
        the first and second connecting elements are attached to proximal ends of corresponding first and second ones of the dental implants, both of said implants being securely fixed at distal ends thereof into operative positions on a member and at a distance from each other, the bar assembly forming a rigid connection with both of the implants;
        each of the first and second connecting elements having an integrally formed construction and having a body, with a partly convex outer surface and a tubular element extending outward from the body so as to define first and second tubular elements respectively, each of the tubular elements having an exposed end and a first bore longitudinally extending inward from said exposed end of said each tubular element, and a second bore, being a through-bore, through said body and the convex surface and oriented substantially perpendicular to said first bore, both of the connecting elements being oriented such that the first and second tubular elements face each other, and the convex surface of the body being complementary to and in abutting contact with a concave surface fixedly associated with a respective one of the implants;
        the rod-shaped element extending between and slideably received in the first bore of each of the tubular elements such that, by slideable direct axial movement of a respective one of the first and second tubular elements along the rod-shaped element, a distance between the opposing ends of the bar assembly can be adjusted by movement of either of the opposing ends of the bar assembly relative to the other; and
        the device further comprising, for each one of the connecting elements, a separate fastening element longitudinally extending through the second bore and into a respective one of the implants, at least one of the fastening elements being pivotable in three dimensions within said fastening element's corresponding second bore prior to securing thereof, so as to fasten a corresponding one of the opposing ends of the bar assembly to said respective one implant, wherein each respective fastening element, once secured into position, closes off said fastening element's corresponding through-bore in the bar assembly coupled therewith such that the bar assembly has a closed outer surface.

2. The device recited in claim 1 wherein the body is at least partially ball-shaped.

3. The device recited in claim 1 wherein the connection is substantially stress-free.

4. The device recited in claim 1 further comprising a coupling element situated between the proximal end of each one of the implants and the body of each respective one of the connecting elements.

5. The device recited in claim 4 wherein the coupling element comprises a concave surface complimentary to and in abutting contact with the convex surface of the body such that both the coupling element and the body can pivot with respect to each other.

6. The device recited in claim 4 wherein the body is ball-shaped, the coupling element is socket-shaped, and the fastening element, extending through the body of the respective one of the connecting elements, has a socket-shaped portion.

7. The device recited in claim 4 wherein the body is spoon-shaped with opposing convex and concave surfaces, and the coupling element and a portion of the fastening element, in abutting contact with said opposing convex and concave surfaces respectively of the body, have concave and convex surfaces complimentary to respectively the convex and concave surfaces of the body such that the body is pivotably moveable between the coupling element and the fastening element.

8. The device recited in claim 1 wherein the bar assembly, during use, forms a substantially straight connection between the two implants.

9. The device recited in claim 1 having a first bar assembly and a second bar assembly, so as to define two separate bar assemblies, pivotally interconnected to a common one of the implants wherein the body of a respective one of the connecting elements located on one end of each of the first and second bar assemblies so as to define first and second bodies, each one of the bodies having a surface, proximal to a common one of the implants, with a complementary shape to a surface on the other one of the two bodies and located remote from the common one implant, such that the two bodies can be pivotably connected onto each other on the common one implant wherein an angle between a longitudinal axis of said common one implant and a longitudinal axis of each of the first and second bar assemblies is separately adjustable for each one of the two respective bar assemblies.

10. The device recited in claim 1 wherein the second bore has an oval cross-sectional shape.

11. The device recited in claim 1 wherein the body of each of the connecting elements is substantially ball-shaped with said second bore extending through a center of the body, and the proximal end of each one of said implants having a cup-shape defining a rim against which a respective ball-shaped body rests closing off said rim.

12. The device recited in claim 1 wherein said second bore through the body of each of the connecting elements has a cross-section and/or shape such that a respective one of the opposing ends of bar assembly can pivot, around the fastening element extending through said second bore into said implant, at least in a plane including a longitudinal axis of the second bore and in a plane perpendicular to said longitudinal axis.

13. The device recited in claim 1 wherein the body of either one of the connecting elements comprises a ball segment, said second bore extending through a portion of said ball segment.

14. The device recited in claim 1 wherein the body of each of the connecting elements comprises a ring-shaped element having said second bore therethrough, the ring-shaped element being provided around a ball-shaped element of the fastening element and enclosed within said second bore such that a bore-defining inner wall of said second bore is in abutting contact with an outer surface of said ball-shaped element, wherein said ring-shaped element can pivot around said ball-shaped element of the fastening element.

15. The device recited in claim 1 wherein two distal ends of the rod shaped element are slideably enclosed within said first and second tubular elements.

16. A device for fastening a dental or prosthesis to two dental implants, comprising:
a substantially rod-shaped bar assembly with first and second opposing ends and having:
first and second connecting elements respectively situated at the first and second ends; and
a rod-shaped element situated between and slideably engaging with each of the connecting elements; and
wherein:
the first and second connecting elements are attached to proximal ends of corresponding first and second ones of the implants, both of said implants being securely fixed at distal ends thereof into operative positions on a member and at a distance from each other, the bar assembly forming a rigid connection with both of the implants;
each of the first and second connecting elements having an integrally formed construction and having a body, with a partly convex outer surface and a tubular element extending outward from the body so as to define first and second tubular elements respectively, each of the tubular elements having an exposed end and a first bore longitudinally extending inward from said exposed end of said each tubular element, and a second bore, being a through-bore, through said body and the convex surface and oriented substantially perpendicular to said first bore, both of the connecting elements being oriented such that the first and second tubular elements face each other, and the convex surface of the body being complementary to and in abutting contact with a concave surface fixedly associated with a respective one of the implants;
the rod-shaped element extending between and slideably received in the first bore of each of the tubular elements such that, by slideable axial movement of a respective one of the first and second tubular elements along the rod-shaped element, a distance between the opposing ends of the bar assembly can be adjusted by movement of either of the opposing ends of the bar assembly relative to the other; and
the device further comprising, for each one of the connecting elements, a separate fastening element longitudinally extending through the second bore and into a respective one of the implants and having a concave surface complimentary to and in abutting contact with the convex surface of the body such that the fastening element and the body can pivot with respect to each other, at least one of the fastening elements being pivotable in three dimensions within said fastening element's corresponding second bore prior to securing thereof, so as to fasten a corresponding one of the opposing ends of the bar assembly to said respective one implant, wherein each respective fastening element, once secured into position, closes off said fastening element's corresponding through-bore in the bar assembly coupled therewith such that the bar assembly has a closed outer surface.

17. A method for fastening a dental prosthesis as recited in claim 1 to two successively located dental implants which are securely fixed in position in a member and at a distance from each other, the method comprising the steps of:
fastening a first end of a bar assembly on a first one of implants by inserting a first fastener through a first bore defined by the bar assembly, the first bore being dimensioned to enable pivotal orientation of the fastener therein in three dimensions prior to said fastening element's securing thereof;
adjusting a length of the bar assembly by slidable direct axial shifting of a rod-shaped element in at least one tubular element within the bar assembly such that a second end of the bar assembly can be placed on a second one of the implants located next to the first implant;
adjusting angles between a longitudinal axis of the bar assembly and a longitudinal axis of each of the implants by pivoting each end of the bar assembly relative to a respective one of the two implants such that the bar assembly is arranged to form a substantially stress-free connection between said two implants; and
fastening the second end of the bar assembly to the second implant by inserting a second fastener through a second bore defined by the bar assembly so that, when both ends of the bar assembly are secured into position in a fastened condition onto the implants, the bores defined by each of the first and second ends of the bar assembly and respectively into the first and second ones of the implants for use in fastening the ends of the bar assembly to the respective implants is closed off, so that, in use, the bar assembly has a closed outer surface, wherein each of said ends of the bar assembly comprises a connection element having an integrally formed construction.

18. A device for fastening an a dental prosthesis to two dental implants, comprising:
a substantially rod-shaped bar assembly with first and second opposing ends and having:
first and second connecting elements respectively situated at the first and second ends; and
a rod-shaped element situated between and slideably engaging by direct axial motion with each of the connecting elements; and
wherein:
the first and second connecting elements are attached to proximal ends of corresponding first and second ones of the dental implants, both of said implants being securely fixed at distal ends thereof into operative positions on a member and at a distance from each other, the bar assembly forming a rigid connection with both of the implants;
each of the first and second connecting elements having an integrally formed construction and having a body, with an outwardly extending tubular element so as to define first and second tubular elements respectively, each of the tubular elements having an exposed end and a first bore longitudinally extending inward from said exposed end of said each tubular element, and a second bore, being a through-bore, through said body and oriented substantially perpendicular to said first bore, both of the connecting elements being oriented such that the first and second tubular elements face each other, each of the first and second connecting elements also being appropriately shaped such that a position of the bar assembly relative to the implants is adjustable by rotation of the bar assembly relative to at least one of the implants;
the rod-shaped element extending between and slideably received in the first bore of each of the tubular elements such that, by slideable direct axial movement of a respective one of the first and second tubular elements along the rod-shaped element, a distance between the opposing ends of the bar assembly can be adjusted by movement of either of the opposing ends of the bar assembly relative to the other; and
through use of a respective fastening element passing through each corresponding second bore, at least one of the fastening elements being pivotable in three dimensions within said fastening element's corresponding second bore prior to securing thereof, each of the connecting elements is made integral with a respective one of the implants in such a way that, once the opposing ends of the bar assembly are secured into position in a fastened condition to the implants, said second bore in each of the connecting elements is closed off by the respective fastening element so that the bar assembly has a closed outer surface.

19. The device recited in claim 18 wherein each of the connecting elements has a substantially ball-shaped body, said second bore extending through a center of said body and said proximal end of each of said implants having a cup shape defining a rim against which said ball-shaped body rests closing off said rim.

20. The device recited in claim 19 wherein said fastening element is a screw, the ball-shaped body being forced against said rim by the screw extending through said second bore and into said each implant, and said screw having a head portion which closes off an end of said second bore facing away from said each implant.

21. The device recited in claim 18 wherein said second bore has a longitudinal axis and a cross-section and/or shape such that a corresponding one of the ends of the bar assembly can pivot around the fastening element at least in a plane including said longitudinal axis and in a plane perpendicular to said longitudinal axis.

22. The device recited in claim 18 wherein the body of one of the connecting elements comprises a ball segment, said second bore extending through a portion of the ball segment.

23. The device recited in claim 18 wherein the body of each of the connecting elements comprises a ring-shaped element having said second bore therethrough, the ring-shaped element being provided around a ball-shaped element of the fastening element enclosed within said second bore such that a bore-defining inner wall of said second bore is in abutting contact with an outer surface of said ball-shaped element, wherein said ring-shaped element can pivot around said ball-shaped element of the fastening element.

24. The device recited in claim 23 wherein said ball-shaped element is a head of a screw, the ball-shaped element and the screw being the fastening element with which each of said ends of the bar assembly is attached to the respective one implant.

25. The device recited in claim 18 wherein two distal ends of the rod shaped element are slideably enclosed within said tubular elements.

26. A device for fastening a dental prosthesis to two dental implants, comprising:
a substantially rod-shaped bar assembly with first and second opposing ends and having:

first and second connecting elements respectively situated at the first and second ends; and a rod-shaped element situated between and slideably engaging with each of the connecting elements; and wherein:

the first and second connecting elements are attached to proximal ends of corresponding first and second ones of the dental implants, both of said implants being securely fixed at distal ends thereof into operative positions on a member and at a distance from each other, the bar assembly forming a rigid connection with both of the implants;

each of the first and second connecting elements having an integrally formed construction and having a body, with an outwardly extending tubular element so as to define first and second tubular elements respectively, each of the tubular elements having an exposed end and a first bore longitudinally extending inward from said exposed end of said each tubular element, and a second bore, being a through-bore, through said body and oriented substantially perpendicular to said first bore, both of the connecting elements being oriented such that the first and second tubular elements face each other, each of the first and second connecting elements also being appropriately shaped such that a position of the bar assembly relative to the implants is adjustable by rotation of the bar assembly relative to at least one of the implants;

the rod-shaped element extending between and slideably received in the first bore of each of the tubular elements such that, by slideable movement of a respective one of the first and second tubular elements along the rod-shaped element, a distance between the opposing ends of the bar assembly can be adjusted by movement of either of the opposing ends of the bar assembly relative to the other;

through use of a respective fastening element passing through each corresponding second bore, at least one of the fastening elements being pivotable in three dimensions within said fastening element's corresponding second bore prior to securing thereof, each of the connecting elements is made integral with a respective one of the implants in such a way that, once the opposing ends of the bar assembly are secured into position in a fastened condition to the implants, said second bore in each of the connecting elements is closed off by the respective fastening element so that the bar assembly has a closed outer surface;

and further wherein:

the body of one of the connecting elements comprises a spoon-shaped segment having opposing concave and convex surfaces;

the respective fastening element is a screw; and the spoon-shaped segment is forced onto the proximal end of the respective one implant by the screw, the screw having an at least partly ball-shaped element with a convex surface having a radius similar to a radius of the concave surface of the spoon-shaped segment.

27. The device recited in claim 26 wherein said ball-shaped element is made integral with the screw.

28. The device recited in claim 26 wherein said spoon-shaped element comprises one of the opposite ends of the bar assembly or of a further bar assembly.

29. A device for fastening a dental prosthesis to two dental implants, comprising:

a substantially rod-shaped bar assembly with first and second opposing ends and having:

first and second connecting elements respectively situated at the first and second ends; and a rod-shaped element situated between and slideably engaging by direct axial motion with each of the connecting elements; and wherein:

the first and second connecting elements are attached to proximal ends of corresponding first and second ones of the dental implants, both of said implants being securely fixed at distal ends thereof into operative positions on a member and at a distance from each other, the bar assembly forming a rigid connection with both of the implants;

each of the first and second connecting elements having an integrally formed construction and having a body, with a partly convex outer surface and a tubular element extending outward from the body so as to define first and second tubular elements respectively, each of the tubular elements having an exposed end and only two bores, comprising a first bore longitudinally extending inward from said exposed end of said each tubular element, and a second bore through said body and the convex surface and oriented substantially perpendicular to said first bore, both of the connecting elements being oriented such that the first and second tubular elements face each other, and the convex surface of the body being complementary to and in abutting contact with a concave surface fixedly associated with a respective one of the implants;

the rod-shaped element extending between and slideably received in the first bore of each of the tubular elements such that, by slideable direct axial movement of at least one of the first and second tubular elements along the rod-shaped element, a distance between the opposing ends of the bar assembly can be adjusted by movement of either of the opposing ends of the bar assembly relative to the other; and the device further comprising, for each one of the connecting elements, a separate fastening element longitudinally extending through the second bore and into a respective one of the implants so as to fasten a corresponding one of the opposing ends of the bar assembly to said respective one implant, at least one of the fastening elements being pivotable in three dimensions within said fastening element's corresponding second bore prior to securing thereof, wherein the fastening element, once secured into position, closes any path into said one of the connection elements such that the bar assembly has a closed outer surface.

* * * * *